United States Patent [19]

Beyleveld et al.

[11] 4,287,371

[45] Sep. 1, 1981

[54] NOVEL PEROXYKETALS DERIVED FROM ALKOXYACETONES

[75] Inventors: Wilhelmus M. Beyleveld, Olst; Lodewijk Roskott, Gorssel, both of Netherlands

[73] Assignee: Akzona Incorporated, Asheville, N.C.

[21] Appl. No.: 87,031

[22] Filed: Oct. 22, 1979

Related U.S. Application Data

[63] Continuation of Ser. No. 923,505, Jul. 10, 1978, abandoned.

[30] Foreign Application Priority Data

Jul. 15, 1977 [NL] Netherlands ............... 7707887

[51] Int. Cl.$^3$ .......................................... C07C 179/093
[52] U.S. Cl. ...................................... 568/563; 568/567
[58] Field of Search ............................... 568/563, 567

[56] References Cited

U.S. PATENT DOCUMENTS 3,686,102  8/1972  Groepper et al. ............ 568/563

FOREIGN PATENT DOCUMENTS

1293771  4/1969  Fed. Rep. of Germany ........... 568/563

*Primary Examiner*—Werren B. Lone
*Attorney, Agent, or Firm*—Francis W. Young; Robert F. Green

[57] ABSTRACT

Novel peroxyketals having the general formula

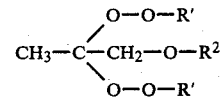

are provided, wherein R' represents a tert.alkyl group having 4–12 carbon atoms and $R^2$ represents a branched or a non-branched alkyl group having 1–12 carbon atoms or a substituted or unsubstituted cycloalkyl group having 5–12 carbon atoms. The peroxyketals can be used to advantage for initiating the copolymerization reaction of ethylenically unsaturated compounds such as unsaturated polyester resins containing both an unsaturated polyester and an ethylenically unsaturated monomer such as styrene.

4 Claims, No Drawings

NOVEL PEROXYKETALS DERIVED FROM ALKOXYACETONES

This is a continuation of application Ser. No. 923,505 filed July 10, 1978 now abandoned.

The invention relates to novel peroxyketals derived from alkoxyacetones and are of the general formula:

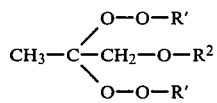

wherein R' represents a tert.alkyl group having 4–12 carbon atoms and $R^2$ a branched or a non-branched alkyl group having 1–12 carbon atoms or a substituted or unsubstituted cycloalkyl group having 5–12 carbon atoms, and to processes for the preparation of these peroxyketals as well as to the application thereof in chemical reactions taking place under the influence of free radicals, more particularly the compression moulding of unsaturated polyester resin moulding compounds. It is known that unsaturated polyester resins can be cured under the influence of free radicals.

By unsaturated polester resins are to be understood solutions of unsaturated polesters in reactive monomers containing one or more $CH_2=CH<$ groups, such as styrene, vinyl toluene, methyl methacrylate, diallylphthalate, and divinyl benzene. The ratio of reactive monomer to unsaturated polyester is generally 30–50% by weight of monomer to 70–50% by weight of polyester.

The unsaturated polyester is obtained by condensation of approximately equivalent amounts of a divalent alcohol, such as ethylene glycol, propylene glycol, diethylene glycol, neopentyl glycol, dipropylene glycol and an unsaturated dibasic carboxylic acid or the anhydride thereof, such as maleic acid, maleic anhydride, fumaric acid, itaconic acid in the presence, if desired, of an aromatic dicarboxylic acid such as phthalic acid or its anhydride, isophthalic acid, tetrachlorophthalic acid or its anhydride, saturated dicarboxylic acids such as malonic acid, adipic acid, sebacic acid, succinic acid and the like.

If such polyester resins are employed as moulding compounds, then it is desirable that they should contain thickeners, more particularly chemical thickeners, such as magnesium oxide and hydroxide or oxides and hydroxides of other metals of the second group of the periodic system. These thickeners are generally added in amounts of 0.5 to 25 parts, and preferably 1 to 5 parts per 100 parts of unsaturated polyester resin. Into the unsaturated polyester resin moulding compounds there may, besides thickeners, be incorporated mould release agents, such as zinc stearate, calcium stearate and polyethylene; fillers, such as calcium carbonate; clay; pigments, such as titanium dioxide, ferric oxide, zinc oxide; shrinkage reducing agents, such as polyvinyl acetate and other thermoplastics; and reinforcing agents, such as glass fibres.

The curing of unsaturated polyester resin moulding compounds can be effected under pressure and at elevated temperature in the presence of radical generating organic peroxides. The known 2,2-ditert.butyl peroxypropane, a peroxyketal derived from acetone or 2-propanone, is not suitable to be used for this purpose because it is too volatile and too hazardous. The peroxyketals derived from alkyl-substituted acetones, such as 2,2-ditert.butylperoxybutane, derived from methylethyl ketone and 2,2-ditert.butylperoxy-4-methylpentane, derived from methylisobutyl ketone are not suitable either, because the moulded articles prepared from polyester resin moulding compounds cured under pressure and at elevated temperature in the presence of the peroxyketals do not display a satisfactory gloss and have a relatively high residual styrene content.

The U.S. Pat. No. 3,686,102 describes β-substituted peroxyketals and the use thereof as initiators in the polymerization of ethylenically unsaturated monomers, as curing catalysts in the curing of unsaturated polyester resins and as curing, cross-linking or vulcanizing catalysts for α-olefinic polymerisates or copolymerisates. Said patent mentions, inter alia, the use of 2,2-di(t-butylperoxy)-4-methoxy-4-methylpentane. This peroxyketal, however, has the disadvantage that the preparation thereof from tert.butylhydroperoxide and 4-methoxy-4-methyl-2-pentanone in an acid medium is readily attended with the formation of carbonium ions, which give rise to undesirable side reactions, as a result of which the yield of the peroxyketal desired is considerably reduced. Moreover, the starting ketone causes skin and eye irritation.

It has now been found that peroxyketals derived from alkoxyacetone which have not been described before and are of the general formula

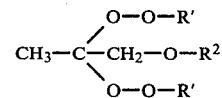

wherein R' represents a tert.alkyl group having 4–12 carbon atoms and $R^2$ a branched or a non-branched alkyl group having 1–12 carbon atoms or a substituted or unsubstituted cycloalkyl group having 5–12 carbon atoms are excellently suitable to be used in reactions carried out under the influence of free radicals, such as the polymerization of unsaturated monomers and the vulcanization of elastomers, more particularly however, in the compression moulding of unsaturated polyester moulding compounds. For it has been found that the moulded products thus obtained have a very good gloss and a very low content of residual monomer. For this purpose the peroxyketals according to the invention may be used in amounts of 0.05–5.0% by weight, and preferably in an amount of 0.2–2.0% by weight, calculated on the amount of unsaturated polyester resin.

The novel peroxyketals according to the invention can be obtained in a simple manner by reacting a hydroperoxide of the formula R'OOH with an alkoxy acetone of the general formula

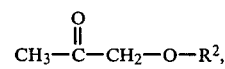

wherein R' and $R^2$ have the above-indicated meaning, in a molar ratio of 2:1, at a temperature in the range of −10° to +50° C., preferably however at a temperature in the range of −5° to 15° C., in the presence of a strongly acid catalyst, such as sulphuric acid, hydrochloric acid, perchloric acid and para-toluene sulphonic acid. If desired, the water evolved during the reaction may be removed by distillation. The peroxyketal formed can be extracted from the reaction mixture in a known manner with the aid of hexane or some other suitable solvent and subsequently isolated by distilling the solvent off under reduced pressure.

As examples of starting hydroperoxides may be mentioned: t.butyl-, t.amyl-, t.octyl-, such as 2,4,4-trimethylphenyl-, and t.dodecylhydroperoxide.

As examples of alkoxyketones may be mentioned: methoxyacetone, ethoxyacetone, n-butoxyacetone, n-hexyloxyacetone, n-octyloxyacetone, n-dodecyloxyacetone, isopropoxyacetone, isobutoxyacetone, 2-ethylhexyloxyacetone, cyclopentyloxyacetone, cyclohexyloxyacetone, 4-tert.butylcyclohexyloxyacetone, cyclooctyloxyacetone, and cyclododecyloxyacetone. The invention will be further described in the following examples, which illustrate the subject invention and are not in limitation thereof. By the term standard resin used in the examples is to be understood a commercial product prepared from 1.2 moles of maleic anhydride, 1 mole of phthalic anhydride, 1.0 mole of diethylene glycol and 1.3 moles of 1,2-propanediol, diluted with about 30% by weight of styrene. To stabilize this produce 0.01% by weight of hydroquinone and 0.01% by weight of para-tert.butylcatechol were added to it. The product has an acid number of 30 and a viscosity at 20° C. of 2,400 mPa.s. To determine the flow of a moulding compound 5 grams of this material were placed between two flat plates and over a period of 60 seconds subjected to a compression moulding load of 1 MPa. at a temperature of 140° C. The resulting diameter of the compression moulded compound is a measure of the flow. The gloss was determined in accordance with DIN 67 530 at an angle of reflection of 45°. The residual styrene content was determined in accordance with DIN 16 945.

EXAMPLE I

Into a 3-neck 250-ml flask provided with a drain cock, a stirrer and a thermometer there were charged 18.9 grams of a 70%-methoxyacetone and 30.9 grams of 93%-tert.butylhydroperoxide. Subsequently, the contents of the flask were cooled down to 0° C., after which over a period of 30 minutes and at a temperature in the range of 0°–5° C., 30.8 grams of 70%-$H_2SO_4$ were added, with stirring. The stirring was continued for 45 minutes at 0° C. To isolate the peroxyketal formed 110 ml of hexane were added to the reaction mixture. After the aqueous lower layer had been drained off, the organic upper layer was washed 5 times with 5 ml of 4 N KOH solution and subsequently with water until neutral.

Finally, the hexane was distilled off under reduced pressure and at a temperature of 20° C. The liquid product obtained weighed 31.6 grams and contained 96.2% of 1-methoxy-2,2-ditert.butylperoxypropane, which was found by determination of the active oxygen content. The structure was confirmed by IR and NMR analyses. Likewise, the following peroxyketals were synthesized and their contents determined.

1-ethoxy-2,2-ditert.butylperoxypropane (content 100%)
1-n.octyloxy-2,2-ditert.butylperoxypropane (content 72.1%)
1-n.dodecyloxy-2,2-ditert.butylperoxypropane (content 81.5%)
1-isopropoxy-2,2-ditert.butylperoxypropane (content 92.3%)
1-(2-ethylhexyloxy)-2,2-ditert.butylperoxypropane (content 75.4%)
1-(cyclohexyloxy)-2,2-ditert.butylperoxypropane (content 64.7%)
1-(4.tert.butylcyclohexyloxy)-2,2-ditert.butyl-peroxypropane (content 68.9%)
1-cyclododecyloxy-2,2-ditert.butylperoxypropane (content 70.5%).

EXAMPLE II

Into a 3-neck 250 ml flask provided with a drain cock, a stirrer and a thermometer there were charged 14.4 grams of a 70%-methoxyacetone and 32.2 grams of 95.1%-2,4,4-trimethylpentyl-2-hydroxyperoxide. Subsequently, the contents of the flask were cooled to 10° C., after which over a period of 15 minutes and at a temperature of 10° C. 24.9 grams of 70%-$H_2SO_4$ were added, with stirring. The stirring was continued for 4 hours at the same temperature. Next, 24.8 grams of water were added. After the aqueous, sulphuric acid-containing layer had been drained off, the organic layer was washed 5 times with 30 ml of 2 N KOH solution and subsequently with water until neutral. Then the organic layer was dissolved in petroleum ether having a boiling point of 48°–60° C., and stirring for 1 hour at 20°–25° C. while adding a solution of 3.1 grams of $Na_2SO_3$ and 0.9 grams of $Na_2S_2O_5$ in 50 ml of water. Next, the aqueous phase was drained off and the petroleum ether evaporated off under reduced pressure. The liquid product obtained weighed 23.2 grams and contained 90.7% of 2,2-bis(2,4,4-trimethylpentyl-2-peroxy)-1-methoxypropane, which was found via determining the active oxygen content. The structure was confirmed by IR and NMR analyses.

EXAMPLE III

Into a 3-neck, 500-ml flask provided with a stirrer, a thermometer and a distillation set up suitable for the azeotropic removal of water, there were charged 58.5 grams of 92%-tert.butylhydroperoxide, 75 grams of toluene, 33.6 grams of 78.4%-methoxyacetone, 3 grams of 4-N sulphuric acid and 2 drops of a defoamer. Subsequently, the mixture was heated to a temperature of 30° C. and the reaction water removed by azeotropic distillation under reduced pressure. After 2 hours, during which 13.2 grams of water had been distilled off, the reaction was completed. Next, the reaction mixture was washed twice with 40 ml of 4-N NaOH and 40 ml of water. There were obtained 156.2 grams of reaction product containing 37% of 1-methoxy-2,2-ditert.butylperoxypropane.

EXAMPLE IV

To a moulding compound of the following composition:
standard resin—30.5 parts by weight
styrene—2.5 parts by weight
zinc stearate—0.5 parts by weight
calcium carbonate—46.0 parts by weight
magnesium oxide—0.5 parts by weight
glass fibres, 6 mm long—20.0 parts by weight
contained in a Z-blade mixer there were added, at a temperature of 20° C., 0.30 parts by weight of 1-methoxy-2,2-ditert.butylperoxypropane. The compound was thickened by leaving it at room temperature for 3 days. Next the flow of the compound was determined, In a steel mould the compound was compressed into a 4 mm thick moulding over a period of 60 seconds at a temperature of 140° C. and a load of 10 MPa. Of the moulding thus obtained the gloss and the residual styrene content were determined.

Corresponding measurements were carried out on moulding compounds containing the same amounts by weight of other peroxyketals according to the invention and on moulding compounds containing the same amounts by weight of the known compounds 2,2-ditert.butylperoxybutane and 2,2-ditert.butylperoxy-4-methyl pentane.

The peroxyketals and the compression times used and the results obtained are listed in the following Table A.

TABLE A

| Peroxyketal | Moulding time (in sec.) | Flow (in cm) | Gloss | Residual Styrene (%) |
|---|---|---|---|---|
| 1-methoxy-2,2-ditert . butylperoxy propane | 30 | | 42 | 0.02 |
| | 60 | 11.6 | 51 | 0.02 |
| | 120 | | 51 | 0.01 |
| 1-ethoxy-2,2-ditert . butylperoxy-propane | 30 | | 40 | 0.04 |
| | 60 | 12.9 | 48 | 0.03 |
| | 120 | | 48 | 0.01 |
| 1-n . octyloxy-2,2-ditert . butylperoxy-propane | 30 | | 35 | 0.07 |
| | 60 | 12.2 | 38 | 0.05 |
| | 120 | | 38 | 0.03 |
| 1-n . dodecyloxy-2,2-ditert . butylperoxy propane | 30 | | 37 | 0.09 |
| | 60 | 13.1 | 41 | 0.07 |
| | 120 | | 42 | 0.05 |
| 1-isopropoxy-2,2-ditert . peroxypropane | 30 | | 36 | 0.10 |
| | 60 | 11.5 | 40 | 0.08 |
| | 120 | | 45 | 0.05 |
| 1-(2-ethylhexyloxy)-2,2-ditert . butyl-peroxypropane | 30 | | 38 | 0.08 |
| | 60 | 13.4 | 38 | 0.04 |
| | 120 | | 45 | 0.03 |
| 1-cyclohexyloxy-2,2-ditert . butyl-peroxypropane | 30 | | 33 | 0.11 |
| | 60 | 12.9 | 50 | 0.08 |
| | 120 | | 45 | 0.03 |
| 1-(4-tert . butyl-cyclohexyloxy) 2,2-ditert . butyl-peroxypropane | 30 | | 40 | 0.07 |
| | 60 | 12.5 | 40 | 0.04 |
| | 120 | | 41 | 0.02 |
| 1-cyclododecyloxy-2,2-ditert . butyl-peroxypropane | 30 | | 32 | 0.11 |
| | 60 | 13.5 | 38 | 0.07 |
| | 120 | | 42 | 0.05 |
| 2,2-ditert . butyl-peroxybutane | 60 | 13.5 | 22 | 0.28 |
| | 120 | | 26 | 0.16 |
| 2,2-ditert . butyl-peroxy-4 methyl pentane | 60 | 13.3 | 30 | 0.25 |
| | 120 | | 31 | 0.13 |

EXAMPLE V

To a moulding compound of the composition described in Example IV contained in a Z-blade mixer there were added at a temperature of 20° C., 0.2 parts by weight of 2,2 bis 2,4,4-trimethylpentyl-2-peroxy)-1-methoxy-propane, calculated on the unsaturated polyester resin. To thicken the compound it was stored for 3 days at room temperature. Subsequently, the flow of the compound was determined. In a steel mould the compound was compressed into a moulding over a period of 60 seconds, at a temperature of 140° C., and a load of 10 MPa. Of this moulding the gloss and the residual styrene content was determined.

Corresponding measurements were carried out on moulding compounds containing different amount by weight of 2,2 bis(2,4,4-trimethylpentyl-2-peroxy)-1-methoxypropane. The amount by weight, the compression times and the results obtained are listed in the following Table B.

TABLE B

| Peroxyketal | Weight (%) | Compression time (in sec.) | Flow (in cm) | Gloss | Residual Styrene content (%) |
|---|---|---|---|---|---|
| 2,2-bis(2,4,4-trimethyl-2-peroxy)-1-methoxypropane | 0.2 | 60 | 14.0 | 44 | 0.39 |
| | | 90 | | 48 | 0.22 |
| | | 250 | | 48 | 0.07 |
| 2,2-bis(2,4,4-trimethyl-2-peroxy)-1-methoxypropane | 0.6 | 60 | 12.9 | 60 | 0.01 |
| | | 90 | | 57 | 0.01 |
| | | 250 | | 58 | 0.002 |
| 2,2-bis(2,4,4-trimethyl-2-peroxy)-1-methoxypropane | 1.0 | 30 | 11.4 | 63 | 0.02 |
| | | 60 | | 66 | 0.004 |
| | | 120 | | 65 | 0.000 |

What is claimed is:

1. Novel peroxyketals having the general formula:

$$CH_3-C\begin{matrix}O-O-R'\\CH_2-OR^2\\O-O-R'\end{matrix}$$

wherein R' represents a tert.alkyl group having 4–12 carbon atoms and R² a branched or non-branched alkyl group having 1–12 carbon atoms or a substituted or unsubstituted cycloalkyl group having 5–12 carbon atoms.

2. Novel peroxyketals according to claim 1, wherein R' represents a

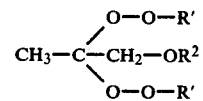 group or a 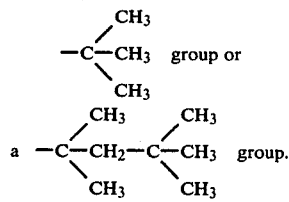 group.

3. Novel peroxyketals according to claim 1, wherein R' represents tert.butyl and R² stands for methyl, ethyl, n-octyl, n-dodecyl, isopropyl, 2-ethylhexyl, cyclohexyl, 4-tert.butylcyclohexyl or cyclododecyl.

4. Novel peroxyketals according to claim 1, wherein R' represents 2,4,4-trimethylpentyl and R² methyl.

* * * * *